United States Patent [19]

Chang

[11] Patent Number: 5,292,867

[45] Date of Patent: * Mar. 8, 1994

[54] CHIMERIC MONOCLONAL ANTIBODIES WHICH BIND TO THE EXTRACELLULAR SEGMENT OF THE MEMBRANE-BOUND DOMAIN OF A HUMAN MEMBRANE-BOUND IMMUNOGLOBULIN

[75] Inventor: Tse W. Chang, Houston, Tex.

[73] Assignee: Tanox Biosystems, Inc., Houston, Tex.

[*] Notice: The portion of the term of this patent subsequent to Jan. 7, 2009 has been disclaimed.

[21] Appl. No.: 3,839

[22] Filed: Jan. 11, 1993

Related U.S. Application Data

[60] Continuation of Ser. No. 817,918, Jan. 6, 1992, abandoned, which is a division of Ser. No. 272,243, Nov. 16, 1988, Pat. No. 5,091,313.

[51] Int. Cl.$^5$ ............................................. C07K 15/28
[52] U.S. Cl. ............................. 530/387.3; 530/387.9; 530/388.73
[58] Field of Search ............ 530/388.1, 388.73, 387.9, 530/387.3

[56] References Cited

U.S. PATENT DOCUMENTS

| | | | |
|---|---|---|---|
| 4,161,522 | 7/1979 | Hamburger | 514/16 |
| 4,171,299 | 10/1979 | Hamburger | 530/329 |
| 4,683,292 | 6/1987 | Hahn | 530/328 |
| 4,714,759 | 12/1987 | Whitaker | 424/85.91 |

OTHER PUBLICATIONS

Harlow et al "Antibodies: A Laboratory Manual" Cold Spring Harbor Lab, 1988. p. 124.
Baniyash et al. for J. Immunol. 14 799–807, 1984.
Hook et al. Fed Proc 46. 1346, 1987.
Hook et al Fed Proc 40. 968, 1981.
Schulman et al. Nature 276:269–270, 1978.
Roberts et al. Nature 328: 731–734, 1987.
Baniyash et al. Env J. Immunol. 17: 1337–1342. Cheng et al. Nature 296:110 (1982).
Word et al. The Embo Journal 2:887–898 (1983).
Blattner et al. Nature 307: 417–422 (1984).
Cushley et al. Nature 298: 77–79 (1982).
Sita et al. J. Immunol. 128: 712–716 (1982).
Lin et al. PNAS USA 78:504–508 1981.
Ishida et al The Embo Journal vol. 1: 117–123, 1982.
Stanworth Mol. Immunol. 21:1183–1190, 1984.
Stanworth et al. Mol. Immunol. 23:1231–1235, 1986.

Primary Examiner—Christine M. Nucker
Assistant Examiner—Chris Dubrule
Attorney, Agent, or Firm—Eric P. Mirabel

[57] ABSTRACT

Antigenic epitopes associated with the extracellular segment of the domain which anchors immunoglobulins to the B cell membrane are disclosed. For IgE, the epitopes are present on IgE-bearing B cells but not basophils or the secreted, soluble form of IgE. The epitope can be exploited for therapy and diagnosis. For example, antibodies or immunotoxins specific for the epitopes associated with the anchor domain of IgE can be used to selectively destroy IgE-bearing lymphocytes, thus blocking IgE-mediated allergic reactions.

2 Claims, 3 Drawing Sheets

Establishing cDNA Library from mRNA
Isolated from a human IgE-bearing mycloma

▼

Screening clones encompassing the
membrane bound segment of ε immunoglobulin

▼

Sequencing the ε membrane bound segment

▼

Determining the mb/ec portion from the comparison
with the known sequence of ε chain of secretory IgE and
membrane bound segments of various immunoglobulin
heavy chains

Fig. 1

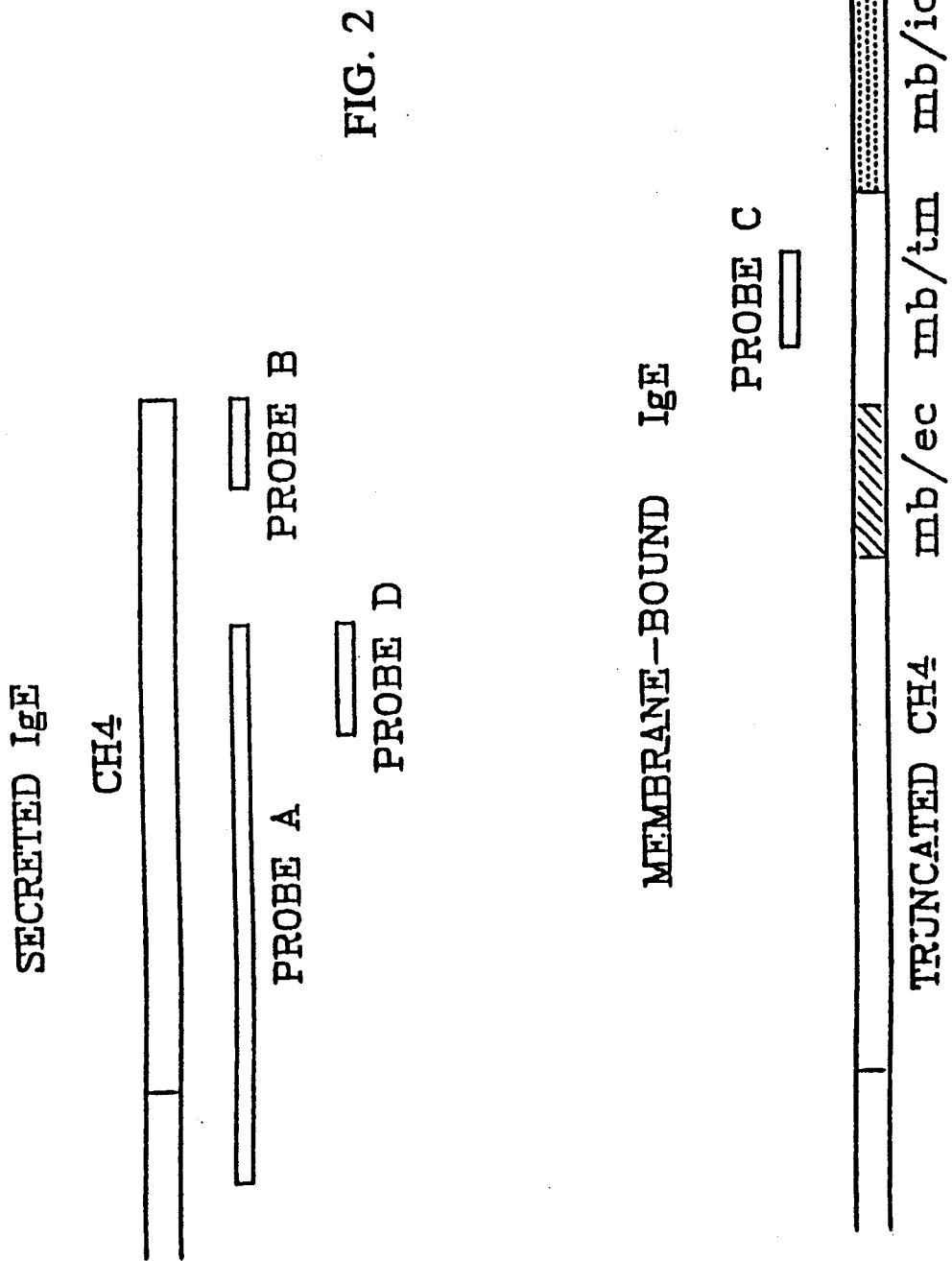

```
                CH4 Domain
       ─────────────────────── TCC CGC TTC TTC GTC TTC
       ─────────────────────── Ser Gly Phe Phe Val Phe probe d
       ├─────────────────────────────────────────────
       AGC CGC CTG GAG GTG ACC AGG GCC GAA TGG GAG
       Ser Arg Leu Glu Val Thr Arg Ala Glu Trp Glu splicing donor
       ──┤
       CAG AAA GAT GAG TTC ATC TGC CGT GCA GTC CAT
       Gln Lys Asp Glu Phe Ile Cys Arg Ala Val His splicing donor
       GAG GCA GCG AGC CCC TCA CAG ACC GTC CAG CGA
       Glu Ala Ala Ser Pro Ser Gln Thr Val Gln Arg probe b
              ├──────────────────────────┤
       GCG GTG TCT GTA AAT CCC GGT AAA TGA
       Ala Val Ser Val Asn Pro Gly Lys End
```

Fig. 3

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
       ( A ) LENGTH: 14 amino acids
       ( B ) TYPE: amino acid
       ( D ) TOPOLOGY: linear ( x i ) SEQUENCE DESCRIPTION: SEQ ID NO:1:

```
Glu Leu Asp Val Cys Val Glu Glu Ala Glu Gly Glu Ala Pro
 1               5                   10
```

CHIMERIC MONOCLONAL ANTIBODIES WHICH BIND TO THE EXTRACELLULAR SEGMENT OF THE MEMBRANE-BOUND DOMAIN OF A HUMAN MEMBRANE-BOUND IMMUNOGLOBULIN

This is a continuation of copending applications Ser. No. 07/817,918 filed on Jan. 6, 1992, which is a divisional of U.S. application Ser. No. 07/272,243, filed Nov. 16, 1988 (now U.S. Pat. No. 5,091,313).

BACKGROUND

The immediate-type hypersensitivity, such as extrinsic asthma, hay fever, and allergic responses to certain food or drugs, is mediated primarily by immunoglobulin E (IgE). In an IgE-mediated allergic response, the allergen binds to IgE on the surface of mast cells and basophilic leukocytes (basophils). This binding causes a crosslinking of the IgE molecules and hence the underlying receptors for the Fc portion of IgE (fcεR) and thereby triggers the release of pharmacologic mediators, such as histamine, slow-reacting substance of anaphylaxis and serotonin. The release of these mast cell and basophil products causes the various pathological manifestations of allergy.

IgE is produced by surface IgE-bearing B lymphocytes (B cells). In individuals sensitized to specific allergens, the allergen-specific IgE is produced by B cells continuously. Recently, Whitaker (U.S. Pat. No. 4,714,759) described a method of treating allergy patients with toxin-conjugated antibodies that were specific for IgE isotype. The intended pharmacological effects of the immunotoxin is to kill IgE-producing B cells.

In the U.S. patent application Ser. No. 140,036 abandoned, filed Dec. 31, 1987 and in its continuation-in-part application Ser. No. 07/226,421, filed Jul. 29, 1988, it was noted that IgE bound to the receptors for the Fc of IgE (FcεR) on the surface of basophils and mast cells very strongly. The association constant, Ka, is in the neighborhood of $1 \times 10^{10}$ liter/mloe and the "off" time is more than 20 hour. Even though IgE is not synthesized by basophils and mast cells, the very strong and stable association of IgE with FcεR means that IgE is virtually always present on these cells. It was indicated in our applications that an immunotherapeutic agent targeting the IgE on B cells must not react with the IgE on basophils and mast cells. Antibodies which react with IgE isotype will cross-link IgE and the underlying FcεR on basophils and mast cells and, when administered in vivo, will induce systemic histamine release leading to anaphylaxis.

In the related patent applications mentioned above the development of monoclonal antibodies that recognized an antigenic epitope present on the IgE on B cells but not on the IgE on basophils was described. In addition, the method of using the antibodies for treating allergy, either in the form of plain antibodies or toxin-conjugated antibodies was described. The plain antibodies can cause the pharmacological mechanism of antibody-dependent cellular cytotoxicity (ADCC) and the toxin-conjugated antibodies can directly cause cytolysis. Both of these mechanisms can lead to the depletion of IgE-bearing B cells without harming the basophils and mast cells. The IgE epitopes present on B cells but absent on basophils were termed ige.bl epitopes (bl stands for B lymphocytes).

SUMMARY OF THE INVENTION

The invention relates to a new class of antigenic ige.bl epitopes (i.e. antigenic epitopes on B cells but not basophils) and the related class of antigenic epitopes which are present generally on B cell membrane-bound immunoglobulins but not on the secreted, soluble form of the immunoglobulin. The invention also pertains to methods of exploiting these newly discovered epitopes for therapeutic and diagnostic purposes.

B cells express on their surface antibody molecules which serve as receptors for antigens during immunological induction. The membrane-bound immunoglobulins differ from the secretory, soluble immunoglobulins synthesized by the same cells in that they have an extra peptidic piece that anchors the them onto the B cell surface. All the ten membrane-bound immunoglobulins on B cells from different species, for which amino acid sequences have been determined, have extra isotype-specific regions that anchor the immunoglobulins to the membrane. These peptidic regions have lengths ranging from 41 to 72 amino acids and can be divided into three segments in terms of locations in relation to the plasma membrane. The middle segments of 25 hydrophobic and uncharged amino acid residues are in the membrane lipid bilayer; the C terminal hydrophilic segments of 3–28 amino acid residues are intracellular; the segments toward N-terminus contain 13 to 27 amino acid residues, are highly acidic and hydrophilic and are on the extracellular surface of the plasma membrane. This part of membrane-bound region of mouse and rat IgE has 19 amino acid residues, among them, 10 are Glu or Asp residues. The length and the hydrophilic and highly charged nature of the extracellular segment indicate that this segment is exposed and accessible to antibodies. These antigenic epitopes located on the extracellular segment of membrane-bound region of immunoglobulin heavy chains can be generally designated mb/ec. The mb/ec segment of IgE can be designated ε.mb/ec segment.

The present invention pertains to the discovery of these mb/ec epitopes, particularly the ε.mb/ec epitopes, and their utility for immunotherapy of allergy. It also pertains to the development of monoclonal and polyclonal antibodies against these epitopes, the use of these antibodies, their immunoconjugates, and their parotope-specific anti-idiotypic antibodies in treating allergy.

BRIEF DESCRIPTION OF THE FIGURES

FIG. 1 outlines the process of determining the sequence of the mb/ec segment of human IgE (ε.mb/ec).

FIG. 2 schematically shows the DNA probes to be used for screening cDNA library for clones containing ε.mb/ec.

FIG. 3 shows the C-terminus of CH4 domain of human ε chain and the locations of probe b and d.

DETAILED DESCRIPTION OF THE INVENTION

1. Unique Antigenic Epitope of IgE as targets of Immunotherapeutic Agents

IgE is present on three cell types in the body, IgE-producing B cells, mast cells, and basophils. If an antigenic epitope of IgE is present on B cells and not on basophils and mast cells, these epitopes (defined as ige.bl) are virtually unique cell surface markers of IgE-bearing B cells. These markers provide for several types of monoclonal or polyclonal antibody-based therapy for IgE-mediated allergic diseases.

2. Anchoring Peptidic piece of B Cell Membrane-bound Immunoglobulins

B cells express on their surface antibody molecules, which serve as receptors for antigens during immunological induction. The membrane-bound immunoglobulins differ from the secretory immunoglobulins synthesized by the same cells in that they have extra peptidic pieces that anchor the immunoglobulin molecules onto the cell surface.

The amino acid sequence data of the ten membrane-bound immunoglobulins from several species have been determined. See Ishida, N. et al., EMBO J., 1:1117 (1982); Steen, M. L. et al., J. Mol. Biol., 177:19–32 (1984); Rogers, J. et al., Cell, 26:19–27 (1981); Yamawaki-Kataoka, Y. et al., proc. Nal. Acad. Sci., MSA, 79:2008–2012 (1982); Kamaromy, M. et al., Nuc. Acids res., 11:6775–6785 (1983); Rogers, J. et al., Cell, 20:303–312 (1980); Bernstein, K>E., J. Emmunol. 132:490–495 (1984); Cheng, H. et al., Nature, 296:410–415 (1982). These sequences indicate certain common features of the plasma membrane bound peptidic piece. As shown in Table 1, the peptidic anchor piece has three segments which are distinguishable based upon their locations in relation to the plasma membrane. Even though these peptidic pieces are short, ranging from 41 to 72 amino acid residues, and have often been referred to as the "membrane-bound domain", the peptides are not entirely in the membrane lipid bilayer. In fact, only 25 amino acid residues, largely hydrophobic residues and threonine and serine residues, located in the middle part of the peptides, are in the lipid bilayer. The C-terminal, hydrophilic segments of 3 to 28 amino acid residues are located on the cytoplasmic side of the membrane. The segments toward the N-terminus, which are connected to the third or fourth constant domains of the immunoglobulin heavy chains ($CH_3$ or $CH_4$) are very hydrophilic and are on the extracellular side of the plasma membrane.

TABLE 1

Key features and properties of peptidic segments unique to membrane-bound immunoglobulins on B cells.

| Immunoglobulin Class/Subclass | First segment | Middle segment | Last segment | Total |
|---|---|---|---|---|
| | Length # Amino acid residues | | | |
| Mouse IgE | 19 | 25 | 28 | 72 |
| Rat IgE | 19 | 25 | 28 | 72 |
| Mouse $IgG_1$ | 18 | 25 | 28 | 71 |
| Mouse $IgG_{2a}$ | 18 | 25 | 28 | 71 |
| Mouse $IgG_{2b}$ | 18 | 25 | 28 | 71 |
| Mouse $IgG_3$ | 18 | 25 | 28 | 71 |
| Mouse IgM | 13 | 25 | 3 | 41 |
| Rabbit IgM | 13 | 25 | 3 | 41 |
| Human IgD | 27 | 25 | 3 | 55 |
| Mouse IgD | 26 | 25 | 3 | 54 |
| Properties | Hydrophilic Highly acidic | Hydrophobic No charged residues | Hydrophilic | |
| Physical Location | On exterior surface | In membrane lipid bilayer | On cytoplasmic surface | |
| Abbreviated Symbols | mb/ec segment | mb/tm segment | mb/ic segment | |

*mb for membrane-bound; ec for extracellular; tm for transmembrane; and ic for intracellular.

The shortest length of the extracellular segment of the membrane-bond pieces of the immunoglobulins (designated mb/ec segments) has 13 amino acid residues (Mouse and rabbit μ chains). The mb/ec segments of all immunoglobulins contain high proportions of charged amino acid residues, almost entirely acidic residues. The proportions of charged amino acid residues and polar hydrophilic residues account for very high percentages of the amino acid composition of the mb/ec segment (Table 2). These parameters indicate that all the mb/ec segments are exposed and long enough to be accessible by antibodies. Studies of the evolution of immunoglobulin heavy chains indicate the ε and γ chains are more related to each other (had more recent common ancestry) than to other chains (Lin, L. C. and Putnam, F. W., Proc. Natl. Acad. Sci. USA, 1981). In addition, the heavy chains evolved before the various mammals species, mice, rats, and humans evolved. Thus, among the ten various mb/ec segments that have been determined, it is probably the murine or the rat ε mb/ec that the human ε mb/ec, which sequence has not yet been reported, will be most related. The next most related will be the γ chains. The murine or rat has 19 amino acid residues, among them 8 Glu and 2 Asp residues. These data also provide support that human ε mb/ec segment is exposed and accessible to antibodies.

TABLE 2

Composition of charged amino acid residues and polar, hydrophilic amino acid residues in the exterior portion of peptidic segments unique to membrane-bound immunoglobulins (mb/ec segments).

| | TOTAL | Acidic residues | Basic residues | Polar residues | Total hydrophilic residues | Proportion of hydrophilic residues % |
|---|---|---|---|---|---|---|
| | # Amino acid residues | | | | | |
| Mouse IgE | 19 | 10 | 0 | 2 | 12 | 63 |
| Rat Ige | 19 | 10 | 0 | 2 | 12 | 63 |

TABLE 2-continued

Composition of charged amino acid residues and polar, hydrophilic amino acid residues in the exterior portion of peptidic segments unique to membrane-bound immunoglobulins (mb/ec segments).

|  | TOTAL | Acidic residues | Basic residues | Polar residues | Total hydrophilic residues | Proportion of hydrophilic residues % |
|---|---|---|---|---|---|---|
| Mouse IgG$_1$ | 18 | 6 | 0 | 4 | 10 | 56 |
| Mouse IgG$_{2a}$ | 18 | 7 | 0 | 2 | 9 | 50 |
| Mouse IgG$_{2b}$ | 18 | 7 | 1 | 1 | 9 | 50 |
| Mouse IgG$_3$ | 18 | 6 | 0 | 4 | 10 | 56 |
| Mouse IgM | 13 | 6 | 0 | 2 | 8 | 61 |
| Rabbit IgM | 13 | 6 | 0 | 1 | 7 | 54 |
| Human IgD | 27 | 6 | 1 | 8 | 15 | 56 |
| Mouse IgD | 26 | 7 | 0.5 | 9 | 16.5 | 63 |

Acidic residues: E (Glu), D (Asp)
Basic residues: K (Lys), R (Arg), H (His); His is partially charged.
Polar residue: S (Ser), T (Thr), C (Cys), Q (Gln), N (Asn)

3. Determining the amino acid sequence of mb/ec segment of human Ig(E ε.mb/ec segment).

A number of well established procedures can be applied to determine the DNA sequence corresponding to the human ε.mb/ec segment. In one approach (FIG. 1), the starting point is the mRNA preparation of a human myeloma cell line which expresses IgE on the surface. SK007 cells can be employed for this purpose. With the mRNA preparation, one can establish a cDNA library employing cloning vector with λ phage or plasmids. A preferred method for constructing the cDNA library is with the cDNA Library Construction System Kit—Librarian I developed and commercialized by Invitrogen (San Diego, Calif.). Stepwise detailed instruction manual is provided for RNA isolation from cells, reverse transcription, second strand synthesis, linker ligation, agarose gel sizing of cDNA, electroelution to purify CDNA<vector ligation, and transformation of E. coli. The vector used in this library is pDCM8.

In the screening of the cDNA library for clones containing the ε.mb/ec segment, several probes can be used. As shown in FIG. 2, the library can be screened with DNA probe a, which is a 1.1 kb long U266 cDNA covering most of length of ε mRNA (no membrane-bound secreted and membrane-bound forms can be distinguished by using additional probes). Probe b is developed by taking advantage of the likelihood that the end of the CH$_4$ domain is truncated in the human ε chain of the membrane-bound form. The truncation occurs whether gene segments of CH$_4$ domain and membrane bound domain are translocated. The loss of C-termini occur with the membrane bound forms of immunoglobulins, including ε and λ, which contain CH$_4$ domains. From the published information on nucleotide sequence of human ε. CH$_4$ doamin, the most probable splicing donor site is intracodon GT, 71 bp 5' of the termination codon TGA. Another GT, which is not intracodon and less likely a splicing donor site, is closer to the terminus (24 bp 5' to the termination codon).

The specific location for probe b is indicated in FIG. 2 and FIG. 3. The probe will react with secreted form of ε chain gene and not membrane form of ε chain gene.

The design of probe c is based on the finding that the transmembrane segment of the membrane-bound domain (mg/tm segment) is very conserved among all the immunoglobulin genes so far sequenced. There is a segment of peptide and its corresponding coding DNA within this mb/tm segment that is nearly identical among all immunoglobulins. FIG. 2 shows the locations of the probe.

Probe d which represents a segment upstream to the most possible splicing donor site, GT, is consisted of 36 bp (FIGS. 2 and 3). This probe should react with ε chain gene of both secreted and membrane-bound forms.

Table 3 summarizes the pattern of reactivities of clones containing ε genes of secreted or membrane-bound forms with the four probes.

TABLE 3

The reactivity of ε gene-containing cDNA clones with probes a, b, c, and d.

|  | ε Secreted | ε Membrane-bound |
|---|---|---|
| Probe a | + | + |
| Probe b | + | − |
| Probe c | − | + |
| Probe d | + | + |

The library size needed to clone the membrane-bound ε chain depends on how abundant the mRNA is. Assuming secreted IgE comprises 0.1% of the SK007 poly A+ RNA, the library size should be about 5,000 independent recombinant clones to have a 99% possibility to isolate a positive clone. In IgE-producing rat immunocytoma IR2 and IR162 cells, mRNA for the membrane-bound form of ε chain was found to be more than 2% of that of the secreted form. Assuming this ratio of membrane-bound/secreted forms of ε chain holds true for the human IgE-producing SK007 cells, the cDNA library size needed to isolate the membrane-bound ε chain is about 250,000. In a preferred procedure, a larger number of clones, about 1,000,000 are screened.

An alternative to the conventional approach of establishing a cDNA library and screening the clones representing the cellular mRNA species is to amplify the mRNA to produce high proportions of their corresponding DNA. The resulting DNA can then be purified by gel electrophoresis and then subjected to sequence analysis. The methodology, referred to as polymerase chain reaction (PCR) amplification, has been established in the past few years and complete system including reagents and equipments have been commercialized. One preferred system is provided by Perkin Elmer Cetus (Norwalk, Conn.). The reagents kit is the GeneAmp DNA Amplification Reagent Kit and the equipment is the DNA Thermal Cycler.

Some of the specific reagents used in this approach are the same as used for the cDNA library cloning. Since no sequence in the membrane-bound segment of the ε chain has been determined, the strategy is to amplify both the secreted and membrane-bound forms of ε chains. Two primers are to be used, one is oligo.dT (25-30-mers) and one is the oligomer corresponding to probe d in FIG. 2 and FIG. 3. Probe d is located 5' to the most possible splicing donor site and therefore primes both the secreted and membrane-bound forms of ε mRNA and DNA. After sufficient amplification, the two populations of DNA fragments are resolved by gel electrophoresis. The secreted form of the ε chain can be distinguished by its reactivity with probe b. The purified DNA's are then subjected to DNA sequencing.

PCR amplification seems to be more efficient procedure than cDNA cloning for mRNA poorly represented in the poly A+ RNA pool. The U266 ε chain cDNA can be used to work out some preliminary annealing conditions between template DNA and oligo-primers.

Another approach for obtaining a DNA clone containing genes encoding the membrane-bound segments is to screen the human genomic DNA library. The human genomic DNA library is readily available. A preferred source is the library constructed using human lung fibroblast WI38 cells provided by Stratogene (La Jolla, Calif.) The genes are in λ vector and the inserted DNA have average sizes of 15K bp. Identification of the clones can be achieved by hybridization with U266 cDNA clone DNA. The location of the gene segment corresponding to the membrane-bound region can be determined by using probe prepared from the homologous mouse gene of the transmembrane segment (probe c of FIG. 2). The sequence of the membrane-bound segment is then determined, and this sequence is shown in the parent application (which has been allowed) Ser. No. 07/272,243, U.S. Pat. No. 5,091,313, filed Nov. 16, 1988, incorporated herein by reference. 3A. The nucleotide sequence of DNA encoding membrane anchoring peptide of human ε chain.

Nucleotide sequence of genomic DNA encompassing the encoding segments for the membrane anchoring peptide of human membrane bound ε chain was determined as described above. The assignment of the exons was made by identifying the nucleotides for splicing donors and acceptors and by comparing to the published homologous sequences of mouse membrane bound ε chain and of immunoglobulins of other classes. Two exons were found to exist.

Human ε.mb/ec peptide is identified as the first fourteen amino acids encoded by membrane exon I. This precedes a stretch of about 25 hydrophobic amino acids which are the transmembrane region. Two possible structures of ε.mb/ec are shown in Ser. No. 07/272,243, U.S. Pat. No. 5,091,313, filed Nov. 16, 1988, and the monomeric structure is SEQ ID NO:1.

As described more fully below, the ε.mb/ec peptide can be used to elicit antibodies which react specifically with membrane bound immunoglobulin ε. For this purpose, the peptides can be chemically synthesized by standard techniques of protein synthesis. A preferred method for synthesizing the peptides is with the RaMPS system (DuPont, Wilmington, Del.), which applies Fmoc chemistry. Alternatively, the proteins can be biosynthesized by employing oligodeoxynucleotides encoding the peptide.

As immunogens, the proteins may be used in either the monomeric or dimeric structural forms shown in Ser. No. 07/272,243, U.S. Pat. No. 5,091,393. Peptides comprising the human ε.mb/ec segment and the connecting four amino acids in the CH4 domain can also be used. In addition, modified peptides having substantial immunological equivalency can be used. For example, the peptide amino acid sequence shown above can be modified by deletion, insertion or substitution of one or more amino acids which do not essentially detract from the immunological properties of the peptide. The peptides can also be used as polymers where the amino acid sequence shown above, or equivalent sequence, is the polymer repeat unit.

4. Developing Antibodies to mb/ec Segment.

The ε.mb/ec peptide can be used in the immunization of animals to prepare polyclonal and monoclonal antibodies. They can also be used to screen for specific monoclonal antibodies or characterize specific polyclonal antibodies. They can also be used to purify monoclonal and polyclonal antibodies.

In the process of preparing for monoclonal antibodies specific for ε.mb/ec peptide, it is not necessary to use the ε.mb/ec peptide in both immunization and antibody identification. For example, in immunizing mice for preparing immune spleen cells for fusion with myeloma cells, the immunogen may be the membrane-bound IgE isolated from plasma membrane of IgE-bearing myeloma cells, such as SK007 cells. The immunogen may also be the IgE-bearing myeloma cells.

For using the synthetic ε.mb/ec peptide as the immunogen, it is more effective to conjugate the peptide to a protein carrier. A preferred protein carrier is keyhole lympit hemocyanin (KLH). If the peptidic segment lacks a Lysine residue or if the Lysine residue is in the middle part of the segment, it is desirable to add a Lysine residue at the C-terminal end. Because the N-terminus already has an α-amino group, the modified synthetic peptidic will have two amino groups for linking. Multiple molecules of peptides can be conjugated to each molecule of the carrier protein. With KLH, a preferred molar ratio for peptide/KLH is 10. The method of conjugation is very well established. Cross-linkers such as glutaraldehyde or bis (sulfosuccinimidyl) suberate or disulfosuccinimidyl tartarate (Catalogue #21579, 20591, Pierce Chemical Co., Rockford, Ill.) have been used. A preferred cross-linker is the latter.

The immunogen, such as the KLH conjugate, can be used to immunize rabbits, goats, rats, or mice to prepare polyclonal antibodies specific for the ε.mb/ec peptide. Lympocytes from the spleen or lymph nodes of immune mice and rats can also be taken to prepare hybridomas secreting monoclonal antibodies specific for the ε.mb/ec peptide. A preferred protocol to prepare the monoclonal antibodies is to fuse immune spleen cells of mice with non-secreting mouse myeloma cells, such as NS-1 or SP2/0 cells using polyethylene glycol.

For optimal immunization of mice, 50 μg of the peptide-KLH conjugate in complete Fruend adjuvant is injected subcutaneously into each mouse for priming. Two and four weeks later, the same amounts of antigen are given s.c. in incomplete Freund's adjuvant. At about the six week time point, the fourth antigen injection is given i.p. in saline. Mice are sacrificed 4 days after the last injection and the spleens are taken for preparing single cell suspension for fusion with myeloma cells. A similar protocol can also be used for immunization with purified native human membrane-bound IgE (having attached membrane anchor domain) isolated from the plasma membrane of IgE-bearing human myeloma cells, such as SK007 cells. When human IgE-bearing cells are used as the immunogen, $1 \times 10^7$ cells are injected i.p. at two week intervals.

The fusion procedure with polyethylene glycol and other various procedures concerning cloning and hybridoma culturing have been well established and the preferred protocol is the same as described by Hudson, L. and Hay. F. C., (*Practical Immunology*, 2nd edition, pp. 303-313, Blackwell Publishing Co., Boston).

The screening of hybridomas for monoclonal antibodies or the identification of polyclonal antibodies or the identification of polyclonal antibodies reactive with ε.mb/ec peptide can be performed with enzyme linked immunosorbent assays (ELISA) using the synthetic ε.mb/ec peptide as the solid phase antigen. An alternative solid phase antigen is the conjugate of ε.mb/ec peptide with a different carrier protein such as bovine serum albumin different from that used in the immunogen. Further characteristics of the monoclonal and polyclonal antibodies are shown in Table 4. The assays employed in these studies are also indicated. The assays have been described in detail in U.S. patent application Ser. Nos. 07/226,421, filed Jul. 29, 1988, and 07/140,036 abandoned, filed Dec. 31, 1987, the teachings of which are incorporated by reference herein.

TABLE 4

The reactivity of antibodies specific for ε.mb/ec peptide with different IgE-containing targets.

| | Reactivity | Assays |
| --- | --- | --- |
| Synthetic ε.mb/ec peptide | + | ELISA |
| Soluble IgE | − | ELISA |
| Basophils & mast cells | − | Immunofluorescence staining Histamine release |
| SK007 myeloma cells | + | Immunofluorescence staining |
| IgE-bearing B cells | + | Immunofluorescence staining |

5. Experiments with Animal Models.

The substances and methods are tested on animal model systems. Two of the most relevant systems are the following:

A. Asthma/rhesus monkey model

The monoclonal antibodies specific for human ε.mb/ec peptide and their related substances of this invention are intended for use to treat patients with various IgE-mediated allergies (see section 6 below). Among these allergies, extrinsic asthma is a more serious form. An experimental model system for studying asthma has been established with rhesus monkeys.

A small portion of rhesus monkeys, which have been infected with the nematode *Ascaris suum*, develop sensitivity to extract of ascaris. When these sensitive monkeys are given spray containing ascaris antigen, they develop breathing problems resembling asthma. Patterson, R., *J. Clini. Invest.* 57:586-593 (1976).

The various substances of this invention can be experimented in the asthma/rhesus monkey model system. The ascaris sensitive monkeys are given the experimental treatment or control treatment and measurements are made to determine:

(a) Do the asthma symptoms upon ascaris challenge decline?

(b) Does the circulating IgE decline?

(c) Do the circulating IgE-bearing B cells decline?

(d) Does the IgE density on basophils decline?

B. Mouse model system

Mice are not known to develop allergic symptoms naturally. However, for demonstrating the pharmacologic mechanisms of the intended therapy in regard to the depletion of IgE-bearing B cells and IgE, the mouse can serve as an excellent model.

The ε.mb/ec segment of mouse has already been sequenced. Ishida, N. et al., *EMBO J.* 1:1117-1123 (1982). The 19 amino acid residue peptide is shown in that publication.

The peptide is synthesized in several forms, including one that has extra Leu-Lys residues at the C-terminus.

The peptide and its KLH conjugate are used as antigens to immunize rabbits and goats. The antisera are collected. The antigen-specific antibodies are purified using column of Sepharose 4B conjugated with the peptide (with Leu-Lys addition) or with peptide linked to bovine serum albumin. Normal mice are injected i.v. or i.p. with the purified antibodies or their related substances to study the following questions:

(a) Does the total IgE in circulation decline?

(b) Does the number of IgE-bearing B cells decline?

(c) Does the density of IgE on the surface of basophils decline?

(d) Do IgM and IgG specific for ε.mb/ec peptide cause different effects? The purpose of this question is to address the effects of antibody dependent cellular cytotoxicity (ADCC) in the depletion of IGE-bearing B cells. IgG, not IgM, is known to mediate ADCC.

6. Therapy of IgE-mediated Allergy based upon Selective Elimination of IgE-producing cells.

Antibodies specific for the ε.mb/ec epitopes bind IgE on the surface of IgE-producing B cells and not on basophils and mast cells. This differential binding of IgE-bearing cell types provides the basis for therapeutic uses of the antibodies.

One of the most powerful agents that trigger the release of pharmacological mediators of allergy from mast cells and basophils is anti-IgE antibody. Conventional anti-IgE antibody will bind IgE on the surface of mast cells and basophils and trigger the release of pharmacological mediators of allergy. The antibodies of this invention cannot bind IgE on these cells.

A. Antibodies specific for IgE-producing cells.

The antibodies specific for ε.mb/ec epitopes in the form of a murine antibody or in the form of mouse/human chimeric antibody, may be applied in several ways for the treatment of IgE-mediated allergies. The antibody can be used as an effector agent mediating an immune function or as a carrier agent of toxins or cytotoxic drugs, as set forth below, for delivering an effector substance.

Antibodies of certain IgG subclasses, such as mouse IgG2a and human IgG1 and IgG3, can mediate antibody-dependent cellular cytotoxicity (ADCC) carried out by certain Fc receptor-bearing phagocytic leukocytes. The antibodies of this invention, especially in the form of mouse gamma 2a antibodies or chimeric antibodies bearing human gamma-1 or gamma-3 chains, can be used to deplete IgE-bearing B cells by the ADCC mechanism. The antibodies can be administered as free antibodies to patients afflicted with IgE-mediated allergy in amounts sufficient to substantially eliminate IgE-producing cells and consequently, to substantially eliminate IgE.

For therapeutic uses described, chimeric or "near-human" antibodies are preferred. Chimeric antibodies comprise a variable or antigen binding (hypervariable or complementarity determining) region derived from an animal antibody and the remaining regions derived from a human antibody. Methods for producing chimeric (e.g. murine/human) antibodies are well established. Chimeric antibodies can be produced in large quantities and they are less immunogenic in humans than nonhuman antibodies. Consequently, they are better suited for in vivo administration, especially when repeated or long term administration is necessary. Antibody fragments of the chimeric antibodies can also be used.

Immunotherapies employing the antibodies of the invention may be used in combination with conventional desensitization immunotherapy. For example, desensitization with allergen may be performed in conjunction with the administration of anti-ε.mb/ec antibodies or immunotoxins (see section C below) to eliminate substantially IgE-producing cells. One major effect of desensitization is that IgGs are induced against the allergen/immunogen. The induction of an IgG response may be most effective when IgE-producing B cells are substantially depleted. The combination of antibody and desensitization therapy is an attractive form of therapy. IgE-producing B cells may be temporarily depleted (for a few weeks or months) by the anti-ε.mb/ec antibody and will eventually repopulate. The desensitization may have longer lasting effects.

B. Immunotherapy combining an ε.mb/ec-specific antibody and a factor enhancing ADCC.

Many factors, such as GM-CSF (granulocyte monocyte-colony stimulation factor) or M-CSF (monocyte-colony stimulation factor), are known to induce the proliferation of leukocytes, including those mediating ADCC. In in vitro experiments, GM-CSF and M-CSF have been shown to augment the ADCC activity on tumor cells mediated by monoclonal antibodies specific for surface antigens expressed on the tumor cells. It is conceivable that the therapeutical effect of ε.mb/ec specific monoclonal antibodies in treating allergies can be enhanced by combining the use of factors that augment ADCC activities.

C. Immunotoxins specific for IgE-producing cells.

Antibodies specific for an ε.mb/ec epitope can be used as immunotoxins specifically targeted to IgE-producing B cells. The immunotoxin binds to IgE-producing B cells but not to mast cells or basophils. In this way, IgE-producing B cells can be selectively eliminated in a patient suffering from an IgE-mediated allergy. The elimination of the Ig producing cells reduces IgE levels in the circulation which results in a reduction of the amount of IgE available to bind mast cells and basophils. The immunotoxin does not kill mast cells or basophils and cause the release of pharmacologic mediators from these cells.

Immunotoxins for selective binding to IgE-producing lymphocytes are comprised of cytolytic or cytotoxic agents conjugated monoclonal anti-ε.mb/ec antibodies. The cytolytic agents can be selected from any of the available substances including ricin, Pseudomonas toxin, diphtheria toxin, pokeweed antiviral peptide, tricathecums, radioactive nuclides, and membrane-lytic enzymes. The antibody and the cytotoxin can be conjugated by chemical or by genetic engineering techniques.

The immunotoxins are administered to a patient afflicted with IgE-mediated allergy in amounts sufficient to reduce or to eliminate IgE-producing lymphocytes in the patient and thereby prevent or alleviate the symptoms of the IgE-mediated allergy. The immunotoxins may be used alone or in combination with free anti-IgE antibody.

7. Antidiotypic Antibodies and Methods of Active Immunization Against ε.mb/ec Epitope.

The ε.mb/ec-specific monoclonal antibodies described thus far can be used to generate parotope-specific, anti-idiotypic antibodies which offer another mode of treating IgE-mediated allergy. Antibodies against the parotope of the ε.mb/ec specific antibodies conformationally resemble the epitope for which the anti-IgE antibody is specific, that is, they resemble an ε.mb/ec epitope. These anti-idiotypic antibodies can be used to actively immunize against ε.mb/ec and induce the endogenous formation of antibodies against the ε.mb/ec epitope. The induced antibodies will mediate the various therapeutical effects of ε.mb/ec specific antibodies.

Because an ε.mb/ec epitope is a "self-molecule", it is not immunogenic. However, active immunization against it may be achieved by using the parotope-specific antibodies of this invention. The parotope-specific antibody shares conformational resemblance with the antigen (which is the ε.mb/ec epitope) which can elicit an immune response in humans against the epitope.

Paratope-specific, anti-idiotypic antibodies are administered to a patient suffering from IgE-mediated allergy in an immunogenic amount to induce the formation of ε.mb/ec antibodies. The anti-idiotypic antibodies are preferably administered as chimeric antibodies. They may also be given as antibody fragments (which also may be chimeric in nature).

8. ε.mb/ec Peptide Analogues and Active Immunization Against ε.mb/ec Epitope.

Even though human ε.mb/ec peptide is probably not immunogenic in humans, a peptide with the same sequence and amino acid substitutions can be immunogenic and induce antibodies that cross react with authentic ε.mb/ec epitope. These ε.mb/ec peptide analogues can be administered to patients suffering IgE-mediated allergies. The antibodies induced by this active immunization can achieve the same functions as the antibodies described in section 6.

9. Diagnostic Uses.

Antibodies against ε.mb/ec epitopes can be used to identify and enumerate IgE-bearing lymphocytes in mixed leukocyte populations. For this purpose, antibodies can be used in standard assay formats for determining cell surface antigens. In general, the antibody is contacted with a sample of the leukocytes to be tested under conditions which allow the antibody to bind IgE-bearing cells in the sample. The cells are then examined for binding of antibody. This can be accomplished by conventional cell staining procedures. For example, a fluorescently labeled second antibody can be used to detect binding of the anti-IgE antibody.

Equivalents

The terms, expressions and examples herein are exemplary only and not limiting, and those skilled in the art will recognize, or be able to ascertain using no more than routine experimentation, many equivalents to the specific embodiments of the invention described herein. Such equivalents are intended to be encompassed by the following claims.

I claim:

1. Chimeric monoclonal antibody which binds to the extracellular segment of the membrane-bound domain of a human membrane-bound immunoglobulin ε chain wherein the antibody's variable and constant regions originated from different species.

2. A chimeric monoclonal antibody of claim 1, having a murine antigen binding region and a human gamma 1 or gamma 3 heavy chain constant region.

* * * * *